(12) United States Patent
Wenger

(10) Patent No.: US 8,352,028 B2
(45) Date of Patent: Jan. 8, 2013

(54) INTRAVASCULAR MEDICAL DEVICE

(75) Inventor: William K Wenger, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 270 days.

(21) Appl. No.: 12/767,176

(22) Filed: Apr. 26, 2010

(65) Prior Publication Data

US 2011/0238077 A1 Sep. 29, 2011

Related U.S. Application Data

(60) Provisional application No. 61/318,062, filed on Mar. 26, 2010.

(51) Int. Cl.
*A61N 1/36* (2006.01)
(52) U.S. Cl. .......................................................... 607/9
(58) Field of Classification Search ................ 607/9, 36, 607/115–116, 119, 126–128, 131
See application file for complete search history.

(56) References Cited

U.S. PATENT DOCUMENTS

| | | | |
|---|---|---|---|
| 3,835,864 A | 9/1974 | Rasor et al. | |
| 4,217,913 A * | 8/1980 | Dutcher | 607/127 |
| 4,721,118 A | 1/1988 | Harris | |
| 6,214,032 B1 | 4/2001 | Loeb et al. | |
| 6,370,434 B1 | 4/2002 | Zhang et al. | |
| 6,697,677 B2 | 2/2004 | Dahl et al. | |
| 7,532,933 B2 * | 5/2009 | Hastings et al. | 607/33 |
| 7,840,281 B2 * | 11/2010 | Kveen et al. | 607/126 |
| 2007/0088418 A1 | 4/2007 | Jacobson | |
| 2007/0150037 A1 | 6/2007 | Hastings et al. | |
| 2008/0039904 A1 | 2/2008 | Bulkes et al. | |
| 2008/0132961 A1 | 6/2008 | Jaax et al. | |
| 2009/0171408 A1 | 7/2009 | Solem | |
| 2009/0198295 A1 | 8/2009 | Dennis et al. | |
| 2009/0248095 A1 * | 10/2009 | Schleicher et al. | 607/2 |

FOREIGN PATENT DOCUMENTS

WO 2006099425 9/2006

OTHER PUBLICATIONS

P0035894.02 (PCT/US2011/029352) PCT Notification of Transmittal of the International Search Report and the Written Opinion of the International Searching Authority.

* cited by examiner

*Primary Examiner* — Carl H Layno
*Assistant Examiner* — Paula J Stice
(74) *Attorney, Agent, or Firm* — Reed A. Duthler

(57) ABSTRACT

An implantable medical device system, including an implantable medical device and an associated implant tool. The device has a hermetic housing containing a power source and electronic circuitry. One or more tines are mounted to the housing movable from a first position extending away from the housing to a second position adjacent the housing. The device is provided with a rotational fixation mechanism. The Implant tool includes an elongated sheath sized to receive the device and provided with internal grooves sized to engage with the tines when the tines are located in their second position. The implant tool may further include a push tool located with the sheath and movable within the sheath to advance the device distally out of the sheath. The sheath may be provided with a closed distal end openable by passage of the device therethrough.

8 Claims, 2 Drawing Sheets

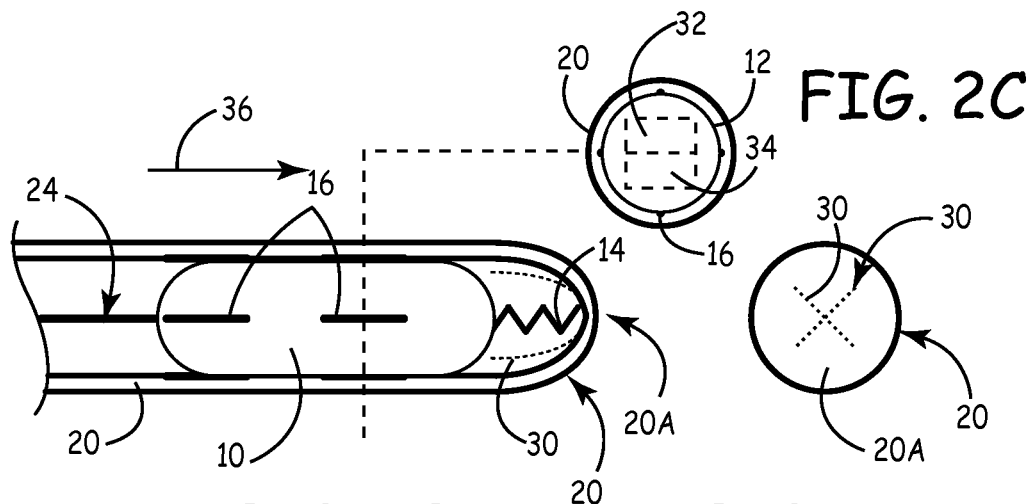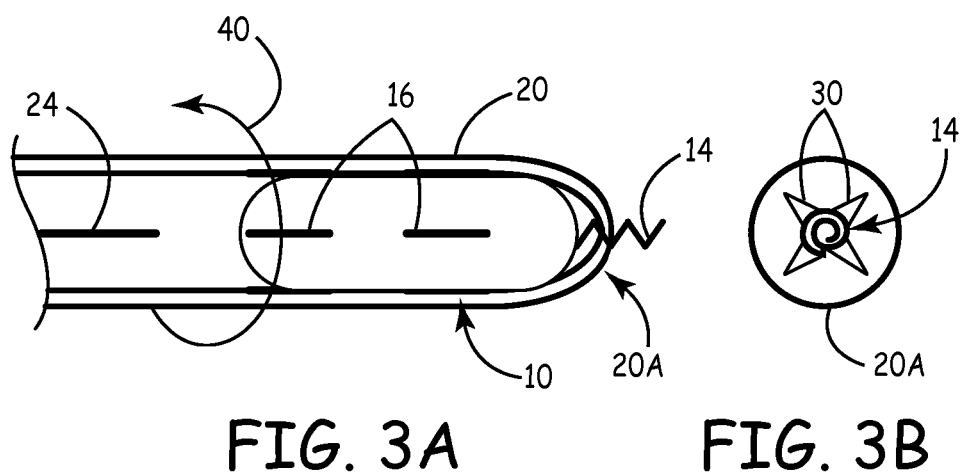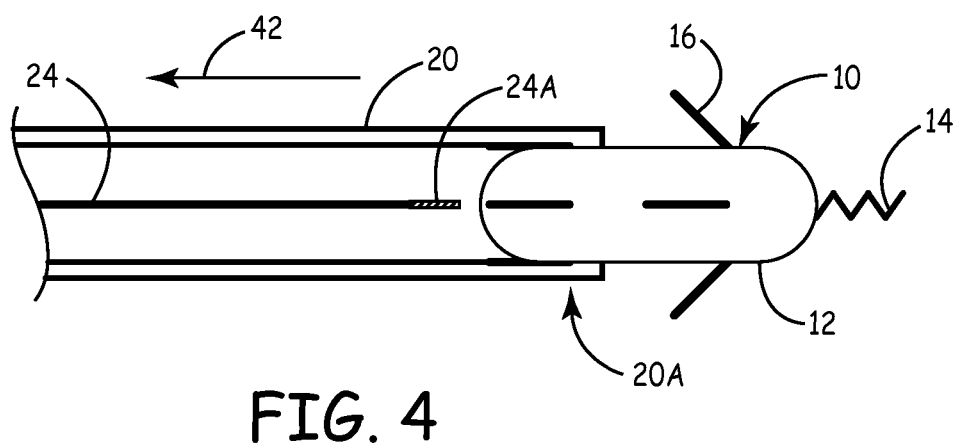

INTRAVASCULAR MEDICAL DEVICE

CROSS-REFERENCE TO RELATED APPLICATIONS

This application claims the benefit of U.S. Provisional Application No. 61/318,062, filed on Mar. 26, 2010. The disclosure of the above application is incorporated herein by reference.

BACKGROUND

1. Field of the Invention

The present invention relates to medical devices and in particular, implantable medical devices.

2. Description of the Related Art

Medical devices related to managing, treating and providing therapy for cardiac conditions have changed and improved dramatically since their inception. Cardiac pacing, as an example, originally required an external pulse generator that itself required external power. While providing life sustaining therapy, patients were tethered to the power source and of course, power failures could prove catastrophic. Portable, battery powered external pulse generators were developed and provided the patient with the ability to be ambulatory; however, the pulse generator had to be carried by the patient. Furthermore, pacing leads were exposed through the patient's tissue and extreme care had to be exercised to minimize the risk of infection or inadvertent withdrawal.

Subsequently, fully implantable, battery powered pulse generators were provided in a hermetically sealed housing. This housing was rather large and was typically implanted in the abdomen of the patient, with leads extending to the heart. The size of such a device often made it rather uncomfortable and the implantation procedure was relatively invasive.

As technology improved, implantable medical devices (IMDs) have become continuously smaller, while offering increased longevity, reliability and many more features and therapies. Epicardial leads that were attached to an external wall of the heart were replaced with endocardial leads that are implanted transvenously, thus becoming minimally invasive. With these smaller devices, the housing was no longer placed in the abdomen but instead was implanted subcutaneously or sub-muscularly, often in the pectoral region. A "pocket" is formed underneath the skin or muscle sufficiently large to receive the housing of the IMD. The exposed or proximal ends of the leads are then connected to the housing and the incision is closed. While now routine, this is still a surgical procedure that requires skill and the appropriate medical facilities.

In general, patients are comfortable with these implanted devices and have a full range of motion, without interference or hindrance. Some patients feel the housing in the "pocket," which may be physically and/or psychologically uncomfortable. Physically, some patients may press against the housing during certain physical activities making the housing noticeable. Even if not a hindrance or painful, simply "feeling" the presence of the device may remind that patient that they have a medical implant and/or medical condition and this alone may be troubling to that patient. Some patients develop a habit of pressing against the pocket and hence against the IMD and often rotating or twisting the IMD. Typically, IMDs that have one or more leads will have any excess lead length coiled under (or around) the housing of the IMD. Thus, frequent patient manipulation may cause portions of the lead(s) to twist or rub, potentially damaging the lead body or pulling the lead out of contact with the targeted tissue. This is sometimes referred to as "twiddlers syndrome."

As the size and capability of IMDs has greatly improved, use of these devices has naturally expanded. This results in greater knowledge and acceptance among the patient population as well as within the medical community. As a result, caregivers are using IMDs with more frequency and for new and diverse purposes. For example, pacemakers are used in patients with various bradyarrhythmias. In such a patient, the heart's intrinsic pacing function fails or is deficient and the IMD provides electrical stimulation to maintain the proper heart rhythm. Such therapy is well known and is referred to above with the early, external pulse generators. Recently, the medical community has been using pacing technology in patient's whose heart rhythm is actually normal. Heart failure patients often have normal rhythm and conduction; however, this disease causes the heart to enlarge. As a result the left and right ventricles are unsynchronized when they contract even though the depolarization waveform triggering such a contraction was "timed" properly. Using cardiac resynchronization therapy (CRT), the left and right ventricles are paced, leading to a mechanical "resynchronization" of the left and right ventricular contractions. This not only leads to better immediate hemodynamic performance, but the heart itself often remodels itself (reducing in size) leading to an improvement in the disease state.

Not only are new therapies and treatments developing, implantable devices are now being used to collect sensor data for a variety of purposes. For example, implantable loop recorders (ILRs) are implanted subcutaneously and record cardiac data, unobtrusively, for extended periods of time. This allows robust medical data to be collected that, as a practical matter, may be otherwise unattainable.

These are merely two examples that illustrate the ever increasing trend to beneficially use implantable medical devices with greater frequency and for a wide variety of purposes that extend well beyond cardiac care. This presents a challenge to some caregivers who might want to use a given device for their patient but do not have the necessary surgical qualifications to actually implant the device. While such a patient may always be referred to another doctor, this adds cost and burden, some patients may not follow through, and some caregivers may simply opt for other treatments in order to maintain their relationship with the patient.

SUMMARY

The present invention is directed toward an implantable medical device, for example a pacemaker, monitor or stimulator for intravascular location. A device according to this invention comprises a hermetic capsule containing the device electronics, and a helix or other rotationally applied attachment mechanism for attaching the capsule to the wall of the heart or other internal organ or structure. The means for delivering the intravascular device comprises a tool that allows the capsule to be screwed into engagement with body tissue such as a heart wall, and then allows the delivery system to be removed without inadvertently unscrewing the device from the body tissue. At the implant site, the device may be employed to provide stimulation, monitor physiologic signals or parameters or to perform other functions.

In most applications of the invention, the device will be placed intravascularly, by inserting the device, contained within its implant tool, into the vasculature in the same manner an intravascular catheter is introduced. The tool and device are then advanced through the vascular system to the point of desired location, typically with the heart or blood vessel. However, in some cases, the device and tool may be advanced though other body passages, such as through the patient' trachea, into the lungs or through the digestive tract. Alternatively, in some applications of the invention, the device and implant tool may be passed through body tissue, for example in the context of a thorascopic surgery procedure or other surgical procedure.

Typically, the delivery tool will comprise a delivery sheath, capable of receiving the capsule. Some preferred embodiments of the invention comprise outwardly extending tines that are part of the capsule. The tines may be fabricated of a resilient material such as an elastomeric polymer. The tines are preferably foldable against the capsule when the capsule is within the delivery sheath, and mate up with recessed grooves on the inner wall of the sheath to allow the sheath to function as a tool for applying rotational torque to the capsule to screw it into body tissue. After the distal end of the delivery sheath is located in the region of the implant area, a push/pull wire running through the sheath is used to push the capsule part way out of the sheath to expose the capsule's helix or other rotational fixation mechanism. The outer sheath may then be used to screw the capsule into the heart wall. Repositioning is possible as long as the tines remain within the sheath. After fixating the capsule in a desired location, the push/pull wire is disconnected from the capsule, and the outer sheath is withdrawn. The elastomeric tines deploy when the sheath is backed away, allowing the tines to engage with trabeculae. The tines serve to prevent the capsule from rotating within the heart, and possibly backing itself out of engagement with heart tissue.

In most embodiments of the invention, the tines will be mounted to the housing so that in a first, relaxed position they extend outward and away from the housing. They are typically resiliently deflectable to a second position alongside the housing, where they can engage the internal grooves within the sheath. However, in some embodiments of the invention, a hinging mechanism may be substituted. Similarly, while in most embodiments of the invention, the rotational fixation mechanism will take the form of a helix, other rotational fixation mechanisms, for example as disclosed in U.S. Pat. No. RE 30,366, issued to Rasor, et al., incorporated herein by reference in its entirety.

BRIEF DESCRIPTION OF THE DRAWINGS

FIG. 2B is a cut-away view through the distal portion of the implant tool of FIG. 2A and illustrating the implantable device of FIG. 1A as located therein.

FIG. 2C is a cross sectional view through the implant tool and device as illustrated in FIG. 2B.

FIG. 2D is an end view of the implant tool.

FIG. 3A is a cut-away view through the distal portion of the implant tool and illustrating the implantable device as located therein showing the fixation helix advanced out of the distal end of the implant tool.

FIG. 3B is an end view of the implant tool and device as illustrated in FIG. 3A.

FIG. 4 is a cut-away view through the distal portion of the implant tool and illustrating the implantable device as located therein showing the fixation helix and the distal set of tines advanced out of the distal end of the implant tool.

DETAILED DESCRIPTION

Figure 1A:
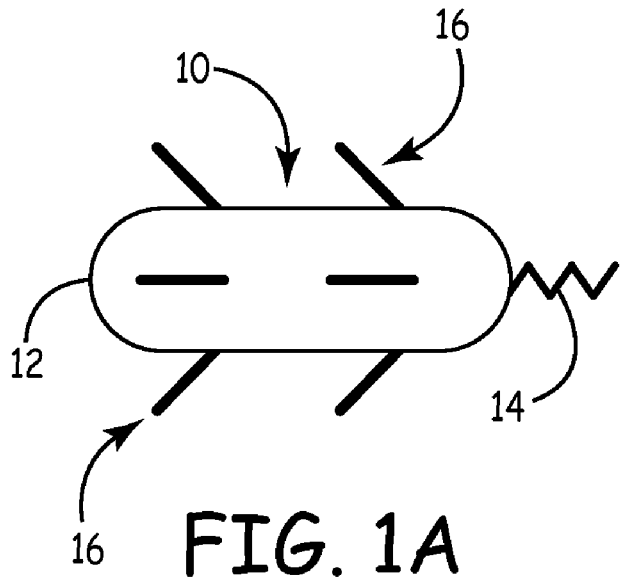
FIG. 1A is a side view of an implantable device according to one embodiment of the invention.

FIG. 1A illustrates an exemplary intravascular medical device (IVMD) 10. The IVMD 10 is an implantable medical device that includes a hermetically sealed housing or capsule 12 containing components to control, power, and operate the device. The housing 12 is shaped and configured to reside entirely within the vasculature anatomy or within a given organ (e.g., the heart, lungs, kidney, pancreas, etc.) via the vasculature. In preferred embodiments, the housing 12 has an approximate diameter of 20 French or less and a volume of 1 cubic centimeter or less. The IVMD 10 may have any number of functional capabilities including sensing, diagnostic, communications and therapy delivery. In the illustrated example, the IVMD 10 includes cardiac sensing and pacing and as well as the ability to communicate with an external device through telemetry. Exemplary descriptions of components for inclusion in such a device are set forth in the above-cited Rasor, et al. patent or in U.S. patent application Publication Ser. No. 12/549,452, by Lund, et al. for an "Elongate Battery for Implatable Medical Device or in U.S. Pat. No. 7,627,376 to Dennis, et al. for an "Intravascular Medical Device", all incorporated herein by reference in their entireties.

A helical fixation member 14 is shown extending distally from the housing 12. In some embodiments, fixation member 14 may be conductive and coupled to the circuitry within the hosing and serve as a sensing and/or pacing electrode. In other embodiments, portions of the housing 12 may serve as and/or carry additional and/or alternative pacing and/or sensing electrodes. Tines 16 may be made of any resilient biocompatible material. In most embodiments, tines 16 will be fabricated of resilient polymers such as silicone rubber or polyurethane. In alternate embodiments, the tines may be fabricated of conductive materials or provided with conductive coatings and may serve as additional or alternative electrodes. The tines should be resilient enough to fold inwardly against the device housing 12 when located in an introducer sheath.

Figure 1B:
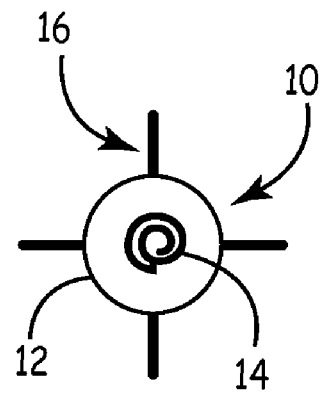
FIG. 1B is an end view of the implantable device of FIG. 1A.

FIG. 1B is an end view of the device of FIG. 1A. Numbered components correspond to identically numbered components in FIG. 1A.

Figure 2A:
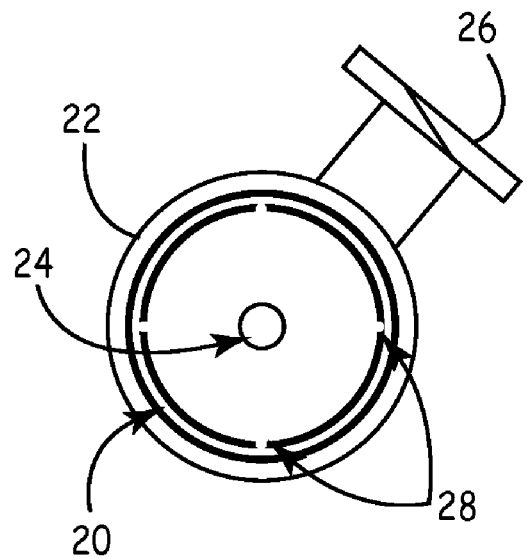
FIG. 2A is a cross sectional view through an implant tool for placing the device according to one embodiment of the invention.

FIG. 2A shows the introducer tool in cross section, looking proximally from a distal portion of the tool. The tool includes a flexible tubular sheath 20, sized to receive the implantable device therein. Sheath 20 may be fabricated of plastic and take the general form of an introducer sheath, having a Luer lock fitting 22 located at its proximal end and optionally a side-arm 26 to allow for flushing or contrast injection.

A push/pull tool 24 is located within the central lumen of the sheath 20, and may be fabricated of metal or plastic, such as stainless steel, Nitinol, nylon, etc. The tool 24 is preferably provided with an engagement mechanism at its distal end to releaseably engage with the proximal end of the device of FIG. 1A. The engagement mechanism may take the form of a mechanical interlock such as a threaded portion on the distal end of the push/pull tool which engages with a corresponding threaded recess in the proximal end of the device of FIG. 1A. Alternatively, magnetic coupling may be provided by means of magnets located on the proximal and distal ends of the device and tool, respectively. In some embodiments, the tool 24 may be used only to push the device of FIG. 1A distally. In such embodiments, no engagement mechanism may be needed. A hemostasis valve may optionally be provided coupled to or as part of the Luer lock fitting 22 to seal around the proximal portion of tool 24.

In at least the distal portion of the sheath 20, longitudinal grooves 28 are provided on the inner wall of the lumen. Grooves 28 are sized to engage with tines 16 (FIG. 1) when the implantable device is loaded therein. The engagement of the tines with the grooves allows for rotational torque to be transferred from the sheath to the implantable device.

FIG. 2B shows the device of FIG. 1A located in the distal portion of the tool of FIG. 2A. Numbered components correspond to identically numbered components in FIGS. 1A and 2A. In this view it can be seen that the distal portion of the sheath resembles the applicator used in conjunction with some brands of tampons, and has a rounded, closed distal end 20A, provided with either slots or weakened lines 30, which allow the distal end 20 to open somewhat in the manner of a blooming flower as the device 10 is pushed proximally in the direction of arrow 36 by tool 24. The tool 24 is used to push the helix 14 out of the distal end of the tool so that it may engage body tissue. If an engagement mechanism is provided, the tool may also be used to pull the device 10 proximally if relocation of the device is needed. The weakened lines 30 may take the form of perforations, grooves or slits extending completely through the distal portion 20A of the sheath. In these cases, the weakened zones define lines of separation between adjacent portions of the closed end which allow expansion and opening of the closed end as the device is advanced distally therethrough. Portions of the sheath 20 may or may not overlap one another when the distal tip is in the closed position.

FIG. 2C is a cross sectional view through the device and tool when arranged as in FIG. 2B. Numbered components correspond to identically numbered components in FIG. 2B. In this view, the power source 32 and circuitry 34 are illustrated schematically. In practical embodiments of the invention the components may be arranged generally as discussed in the Rasor, et al. Lund, et al. or Dennis, et al. patents, cited above.

FIG. 2d shows the distal end 20A of the sheath in the closed position. Weakened lines 30 are illustrated as taking the form of two orthogonally intersecting lines. A greater or lesser number of weakened lines may be provided.

FIG. 3A illustrates the implantable device and implant tool of FIG. 2A, showing the device 10 pushed distally within the sheath 20 by means of tool 24 so that the helix 14 protrudes from the distal end of sheath 20. By rotating the sheath 20 in the direction of arrow 40, the helix may be screwed into body tissue at the desired implant site. Conversely, if repositioning is needed, rotation of the sheath in the opposite direction can unscrew the helix from the tissue. As discussed above, torque is transferred to the device 10 by means of the groves within the sheath 20, which engage the tines 16.

FIG. 3B is an end view of the device and implant tool as illustrated in FIG. 3A. In this view, distal portion 20A of the sheath has separated along the weakened lines 30 and has begun to open.

FIG. 4 shows the device and the implant tool of FIG. 3A with the device moved further distally with respect to the sheath so that the device housing 20 has begun to exit the distal portion 20A of the sheath. This movement is accomplished after the helix 14 has been screwed into body tissue at the implant site and is accomplished by pulling the sheath 20 proximally over the device 10. In this view, the distal tines 16 have exited the sheath and have resiliently moved outward. If the device 10 is located in an area of the heart that contains trabeculae, the tines will engage the trabeculae to prevent rotation of the device and unscrewing of the helix. The push/ pull tool 24 is shown disengaged from the device 10, in this case by unscrewing a threaded distal portion 24A of the device from a corresponding threaded bore in the proximal end of the device 10. The interaction of the grooves within the sheath 20 and the tines also serves to prevent rotation of the device during unscrewing of the tool 24. The sheath 20 and tool 24 may then be pulled proximally to completely disengage the implant tool and allow its removal from the patient's body.

The above-disclosed embodiment of the invention is intended to be exemplary, rather than limiting with regard to the scope of the invention. The scope of the invention is defined by the claims set forth below.

In conjunction with the above disclosure, I claim:

1. An implantable medical device system, comprising:
an implantable medical device comprising:
a hermetic housing containing a power source and electronic circuitry, one or more tines mounted to the housing movable from a first position extending away from the housing to a second position adjacent the housing and a rotational fixation mechanism; and
an implant tool, comprising an elongated sheath sized to receive the device and provided with internal grooves sized to engage with the tines when the tines are located in their second position; and
wherein the implant tool further comprises a push tool located with the sheath and movable within the sheath to advance the device distally out of the sheath.

2. A system according to claim 1 wherein the push tool comprises means for releaseably engaging the medical device.

3. An implantable medical device system, comprising:
an implantable medical device comprising:
a hermetic housing containing a power source and electronic circuitry, one or more tines mounted to the housing movable from a first position extending away from the housing to a second position adjacent the housing and a rotational fixation mechanism; and
an implant tool, comprising an elongated sheath sized to receive the device and provided with internal grooves sized to engage with the tines when the tines are located in their second position; and
wherein the sheath comprises a closed distal end openable by passage of the medical device therethrough.

4. A system according to claim 3 wherein the distal end of the sheath comprises weakened zones between adjacent portions of the distal end.

5. A method of implanting a medical device system, comprising:
inserting an implantable medical device into an implant tool, wherein;
the medical device comprises a hermetic housing containing a power source and electronic circuitry, one or more tines mounted to the housing movable from a first position extending away from the housing to a second position adjacent the housing and a rotational fixation mechanism; and
the implant tool comprises an elongated sheath sized to receive the device and provided with internal grooves sized to engage with the tines when the tines are located in their second position, wherein the implant tool further comprises a push tool located with the sheath and movable within the sheath to advance the device medical distally out of the sheath; and
advancing the device distally out of the sheath using the push tool.

6. A method according to claim 5, wherein the push tool comprises means for releaseably engaging the medical device, comprising disengaging the device from the push tool.

7. A method of implanting a medical device system, comprising:

inserting an implantable medical device into an implant tool, wherein;

the medical device comprises a hermetic housing containing a power source and electronic circuitry, one or more tines mounted to the housing movable from a first position extending away from the housing to a second position adjacent the housing and a rotational fixation mechanism; and the implant tool comprises an elongated sheath sized to receive the device and provided with internal grooves sized to engage with the tines when the tines are located in their second position; and advancing the medical device to a desired implant location using the implant tool; and wherein the sheath comprises a closed distal end openable by passage of the medical device therethrough, comprising opening the distal end by passage of the device therethrough.

8. A method according to claim 7, wherein the distal end of the sheath comprises weakened zones between adjacent portions of the distal end, comprising separating the adjacent portions of the distal end by passage of the device therethrough.

* * * * *